United States Patent
Iga et al.

(10) Patent No.: US 11,305,065 B2
(45) Date of Patent: Apr. 19, 2022

(54) INJECTOR

(71) Applicant: DAICEL CORPORATION, Osaka (JP)

(72) Inventors: Hiromitsu Iga, Hyogo (JP); Yuzo Yamamoto, Hyogo (JP)

(73) Assignee: Daicel Corporation, Osaka (JP)

( * ) Notice: Subject to any disclaimer, the term of this patent is extended or adjusted under 35 U.S.C. 154(b) by 122 days.

(21) Appl. No.: 16/626,285

(22) PCT Filed: Jun. 27, 2018

(86) PCT No.: PCT/JP2018/024467
§ 371 (c)(1),
(2) Date: Dec. 23, 2019

(87) PCT Pub. No.: WO2019/004323
PCT Pub. Date: Jan. 3, 2019

(65) Prior Publication Data
US 2020/0114083 A1 Apr. 16, 2020

(30) Foreign Application Priority Data
Jun. 27, 2017 (JP) .............................. JP2017-125673

(51) Int. Cl.
*A61M 5/30* (2006.01)
*A61M 5/20* (2006.01)
(52) U.S. Cl.
CPC ............ *A61M 5/30* (2013.01); *A61M 5/2046* (2013.01)
(58) Field of Classification Search
CPC ............ A61M 5/2046; A61M 5/31578; A61M 5/3234; A61M 2005/206; A61M 5/30
See application file for complete search history.

(56) References Cited

U.S. PATENT DOCUMENTS 2,322,245 A * 6/1943 Lockhart ................. A61M 5/30
604/69
6,666,843 B1 * 12/2003 Alexandre .............. A61M 5/30
604/68
(Continued)

FOREIGN PATENT DOCUMENTS

EP 3750579 A1 12/2020
JP 2003-534839 A 11/2003
(Continued)

OTHER PUBLICATIONS

Extended European Search Report dated Oct. 7, 2020 in European Application No. 13825152.4, in 7 pages.
(Continued)

*Primary Examiner* — Bhisma Mehta
*Assistant Examiner* — Robert F Allen
(74) *Attorney, Agent, or Firm* — Knobbe Martens Olson & Bear LLP

(57) ABSTRACT

An injector includes an encapsulating portion configured to encapsulate a substance intended for injection, a first application portion configured to combust ignition charge and discharge a combustion product thereby applying a primary ejection energy to the substance intended for injection that is encapsulated in the encapsulating portion, an energy accumulation portion configured to accumulate an energy to be further applied to the substance intended for injection, the energy being different from the primary ejection energy applied by the first application portion. The injector also includes a second application portion configured to release the energy accumulated in the energy accumulation portion by using the discharged combustion product thereby applying, as a secondary ejection energy, the released energy to the substance intended for injection. With this configuration, the substance intended for injection can be caused to suit-
(Continued)

ably reach the target region without affecting the substance intended for injection to be ejected.

10 Claims, 7 Drawing Sheets

(56) References Cited

U.S. PATENT DOCUMENTS

| | | | |
|---|---|---|---|
| 2002/0151842 A1* | 10/2002 | Gonnelli | A61M 5/30 604/70 |
| 2002/0161329 A1 | 10/2002 | Gonnelli et al. | |
| 2003/0135155 A1 | 7/2003 | Alexandre et al. | |
| 2004/0140656 A1* | 7/2004 | Blackburn | B60R 21/268 280/737 |
| 2005/0010167 A1 | 1/2005 | Alexandre et al. | |
| 2006/0281175 A1 | 12/2006 | McSwiggen et al. | |
| 2008/0132450 A1 | 6/2008 | Lee et al. | |
| 2008/0214997 A1 | 9/2008 | Alexandre et al. | |
| 2010/0040619 A1 | 2/2010 | Li et al. | |
| 2013/0237951 A1* | 9/2013 | Oda | A61M 5/30 604/500 |
| 2015/0265770 A1 | 9/2015 | Yoh | |
| 2017/0036901 A1 | 2/2017 | Kuroda et al. | |
| 2018/0036485 A1 | 2/2018 | Oda | |
| 2018/0056003 A1 | 3/2018 | Oda | |
| 2019/0151552 A1 | 5/2019 | Oda | |

FOREIGN PATENT DOCUMENTS

| | | |
|---|---|---|
| JP | 2005-523679 A | 8/2005 |
| JP | 2007-525192 A | 9/2007 |
| JP | 2008-508881 A | 3/2008 |
| JP | 2008-206477 A | 9/2008 |
| JP | 2010-503616 A | 2/2010 |
| JP | 2012-061269 A | 3/2012 |
| JP | 2015-202754 A | 11/2016 |
| WO | WO 01/047586 | 7/2001 |
| WO | WO 03/004620 A2 | 1/2003 |

OTHER PUBLICATIONS

International Search Report and Written Opinion dated Oct. 2, 2018 in International Application No. PCT/JP2018/024467, in 8 pages (with English translation in 9 pages).

Search Report in counterpart European Patent Application No. 19750340.2 dated May 27, 2021.

* cited by examiner

INJECTOR

CROSS REFERENCE TO RELATED APPLICATIONS

This application is a U.S. National Phase of International Application No. PCT/JP2018/024467, filed on Jun. 27, 2018, which claimed priority to and the benefit of Japanese Patent Application No. 2017-125673 filed on Jun. 27, 2017, each of which is hereby incorporated by reference in their entireties.

FIELD

The present invention relates to an injector that injects a substance intended for injection to a target region.

BACKGROUND

As an injector that injects an injection solution to a target region, a needleless injector that performs injection without an injection needle can be exemplified. In some cases, the needleless injector employs a configuration of ejecting an injection solution by applying a pressure to a storing chamber that stores the injection solution. However, the needleless injector having a known configuration in the related art does not exhibit satisfactory repeatability of an injection amount or a depth of the injection solution, and hence it is hard to say that the needleless injector is now widely used.

In view of this, a technique has been disclosed, which adjusts an ejection pressure of the injection solution at a plurality of stages through use of a powder propellant, which is a powder mixture formed of two kinds of powder including high-speed combustion powder and low-speed combustion powder (for example, see Patent Document 1). Specifically, combustion of the high-speed combustion powder first applies a large force to a piston, whereby the injection solution is ejected. As a result, the injection solution penetrates a skin of a human or the like, and is sent into a human body. After that, combustion of the low-speed combustion powder continuously applies a pressure at which the injection solution can be spread in the skin.

CITATION LIST

Patent Document

[Patent Document 1] JP 2003-534839 A

SUMMARY

Technical Problem

When an injection is performed to a target region, it is necessary to accurately deliver a component contained in the injection solution into a part of the target region, which is a destination of the delivery, in accordance with an injection purpose. For example, when an injection solution containing a predetermined medical agent, which is a substance intended for injection, is to be delivered into a skin of a human, the injection solution needs to be ejected after sufficiently considering which part of the skin the medical agent needs to be delivered into, by taking into account that the skin has a layered structure including epidermis, dermis, and subcutaneous tissue, in the order, from a surface side thereof.

Here, when a powder propellant is used as an energy source that applies an ejection pressure of the injection solution as in the related art, the powder propellant needs to be combusted such that a pressure is applied to the injection solution. When the powder propellant is combusted, a constant amount of residue is generated due to a combustion reaction in some cases. Contact between such residue and the substance intended for injection preferably needs to be regulated for hygienic reasons. However, a combustion product (combustion gas) generated by the combustion of the powder propellant has a high pressure, and hence it is not easy to completely prevent contact between the combustion product and the substance intended for injection in the injector.

Thus, in view of the above-mentioned problem, the present invention has an object to provide, to an injector that injects a substance intended for injection to a target region, a technique of causing the substance intended for injection to suitably reach the target region without affecting the substance intended for injection to be ejected.

Solution to Problem

In order to solve the above-mentioned problem, an aspect of the present invention employs a configuration in which two application portions apply an ejection energy to a substance intended for injection to be ejected. Moreover, only one of the application portions uses an energy generated by combustion of an explosive as the ejection energy, and the other application portion applies an ejection energy to the substance intended for injection without using a combustion reaction of the explosive. By suppressing in this way a combustion timing of the explosive, an impact of a residue, generated by combustion of the explosive, on the substance intended for injection is intended to be suppressed as much as possible.

Specifically, according to an embodiment of the present invention, an injector is provided that injects a substance intended for injection to a target region, and that includes an encapsulating portion configured to encapsulate the substance intended for injection, a first application portion configured to combust ignition charge and discharge a combustion product, thereby applying a primary ejection energy to the substance intended for injection that is encapsulated in the encapsulating portion; an energy accumulation portion configured to accumulate an energy to be further applied to the substance intended for injection, the energy being different from the primary ejection energy applied by the first application portion, and a second application portion configured to release the energy accumulated in the energy accumulation portion by using the combustion product that is discharged, thereby applying, as a secondary ejection energy, the energy that is released to the substance intended for injection.

In the injector according to an embodiment of the present invention, the first application portion and the second application portion apply the ejection energy to the substance intended for injection encapsulated in the encapsulating portion such that the substance intended for injection is ejected to the target region. Note that the injector according to an embodiment of the present invention may include an injection needle that is inserted into the target region and guides the substance intended for injection when ejecting the substance intended for injection, or may not include the injection needle. "Ejection" in the present application indicates an action in which the substance intended for injection flows out to the target region from the injection needle in a case where the injector includes the injection needle or from an ejection part or the like provided on the injector side in a case where the injector does not include the injection needle. Here, examples of the substance intended for injection ejected by the injector according to an embodiment of the present invention may include a substance including a component expected to have effects in the target region or a component expected to exert a predetermined function in the target region. Thus, as long as at least ejection by the ejection energy described above can be achieved, a physical mode of the substance intended for injection may be in a state of being dissolved in liquid, or may be in a state of simply being mixed without being dissolved in liquid. As one example, the predetermined substance to be delivered includes vaccine for intensifying an antibody, protein for cosmetic enhancement, a cultured cell for hair regeneration, and the like, and is included in a liquid medium in an electable manner. The substance intended for injection is formed in this way. Note that the medium is preferably a medium that does not hinder the above-mentioned effect and function of the predetermined substance in a state of being injected into the target region. As another method, the medium may be a medium that exerts the above-mentioned effect and function by acting together with the predetermined substance in the state of being injected into the target region.

Here, the first application portion applies the primary ejection energy, and the primary ejection energy is generated from the combustion product generated by combustion of the ignition charge. The ejected substance intended for injection needs to penetrate the surface of the target region such that the substance intended for injection is ejected from the injector to the target region to be delivered into the inside thereof. Thus, at an ejection initial state, the substance intended for injection needs to be ejected to the target region at a relatively high speed. In view of this point, the primary ejection energy is preferably applied using the combustion product discharged by combustion of the ignition charge. Note that, as the ignition charge, there may be employed any one of an explosive containing zirconium and potassium perchlorate, an explosive containing titanium hydride and potassium perchlorate, an explosive containing titanium and potassium perchlorate, an explosive containing aluminum and potassium perchlorate, an explosive containing aluminum and bismuth oxide, an explosive containing aluminum and molybdenum oxide, an explosive containing aluminum and copper oxide, an explosive containing aluminum and iron oxide, or an explosive composed of a combination of a plurality of the explosives of the above. As characteristics of the above-mentioned ignition charge, the combustion product is gas at a high temperature but does not include a gas component at a room temperature, hence the combustion product is condensed immediately after the ignition. As a result, the first application portion can apply the primary ejection energy in an extremely short period of time.

Meanwhile, the second application portion releases the energy accumulated in the energy accumulation portion, and applies the released energy as the secondary ejection energy to the substance intended for injection. Accumulation of the energy in the energy accumulation portion may be performed in a releasable mode. Note that, in an embodiment of the present invention, release of the energy indicates application of the energy, which is already accumulated in a state of being capable of being applied to the substance intended for injection as the ejection energy, to the substance intended for injection. A mode of causing a chemical reaction that generates a new product at the time of applying the ejection energy does not correspond to the release of the energy according to the present invention. Therefore, the second application portion preferably applies the secondary ejection energy to the substance intended for injection with no predetermined chemical reaction with the combustion product that is discharged.

Moreover, for releasing the energy accumulated in the energy accumulation portion, the combustion product discharged by combustion of the ignition charge is used. Therefore, application of the secondary ejection energy by the second application does not precede the application of the primary ejection energy by the first application portion, and, in other words, is performed with application of the primary ejection energy by the first application portion as a trigger. Thus, as described above, it is considered that the primary ejection energy mainly has a significance as an energy that causes the substance intended for injection to penetrate the surface of the target region and to advance inside the target region, and that, in contrast, the secondary ejection energy mainly has a significance as an energy that substantially delivers most of the substance intended for injection into the target region after the penetration through the surface of the target region. Therefore, it is considered that application of the secondary ejection energy by the second application portion has a relatively large action on the substance intended for injection.

However, as described above, the secondary ejection energy by the second application portion releases the energy accumulated in the energy accumulation portion, and does not generate a combustion residue unlike a combustion reaction of an explosive. Thus, in the configuration in which the second application portion applies the secondary ejection energy, there is no occurrence of the substance intended for injection being exposed to the combustion residue. Even if application of the primary ejection energy by the first application portion is also taken into account, it can be said that exposure of the substance intended for injection to a high-temperature environment or to the combustion residue is greatly. As a result, degradation in quality of the substance intended for injection, exposure to the combustion residue, and the like do not occur, and the substance intended for injection can reach the target region suitably.

Here, in the injector described above, the application of the secondary ejection energy by the second application portion may be caused by breakage of a part of the energy accumulation portion by the combustion product that is discharged. That is, with a physical action by which the discharged combustion product breaks a part of the energy accumulation portion, the accumulated energy is discharged and the second application portion applies that energy as the secondary ejection energy to the substance intended for injection. With such configuration, the occurrence of the substance intended for injection being exposed to a combustion residue can be suitably prevented.

Further, in the injector described above, an ejection pressure of the substance intended for injection, which is defined as a pressure of the substance intended for injection ejected from the injector, may be raised to a first peak pressure by application of the primary ejection energy by the first application portion after the energy application is started, and then lowered to a pressure lower than the first peak pressure, and moreover raised again to a second peak pressure by application of the secondary ejection energy by the second application portion. It is considered that the first peak pressure is mainly a characteristic pressure that is required when the initially ejected substance intended for injection penetrates the surface of the target region and advances inside the region, and that the second peak pressure that occurs thereafter is mainly a characteristic pressure that is required when most of the substance intended for injection is delivered into the target region. Note that the ejection pressure is defined as a pressure of the substance intended for injection ejected from an ejection port, which is a pressure applied to the substance intended for injection immediately after ejection from the ejection port, that is, in the vicinity of the ejection port, and a pressure required for ejecting the substance intended for injection from the ejection port. In a physical sense, as a distance from the ejection port extends longer due to ejection, a pressure applied to the substance intended for injection becomes smaller. In an embodiment of the present invention, the ejection pressure is a pressure applied to the substance intended for injection at a time when the substance intended for injection is ejected from the injector to the target region.

Here, specific four triodes of the injector described above are exemplified below. In a first mode, the above-mentioned injector may further include a piston portion configured to advance in a body of the injector and disposed to be able to apply a pressure to the substance intended for injection that is encapsulated in the encapsulating portion. The energy accumulation portion may include a filling space that is filled with a compressed gas that is compressed to a predetermined pressure, and a plate member that prevents contact between the compressed gas in the filling space and the piston portion and that is configured to be broken by the combustion product that is discharged. In this case, as the combustion product that is discharged may break the plate member, the compressed gas filled in the filling space may be discharged to an outside of the filling space and come into contact with the piston portion, such that application of the secondary ejection energy by the second application portion may be performed.

In the first mode, in a state in which the plate member prevents the compressed gas from being in contact with the piston portion, the energy of the compressed gas is accumulated in the filling space. Moreover, the discharged combustion product breaks the plate member, whereby, the accumulated energy is released and is applied as the secondary ejection energy to the substance intended for injection due to contact between the compressed gas and the piston portion. In this application mode, occurrence of the exposure of the substance intended for injection to impurities, such as a combustion residue, is suitably prevented.

Next, in a second mode, the above-mentioned injector may further include a piston portion configured to advance in a body of the injector and disposed to be able to apply a pressure to the substance intended for injection that is encapsulated in the encapsulating portion. The energy accumulation portion may include a filling space that is filled with a compressed gas that is compressed to a predetermined pressure, and a regulation member configured to regulate advancement of the piston portion to the substance intended for injection. In this case, before application of the primary ejection energy by the first application portion, the compressed gas in the filling space may come into contact with the piston portion, and advancement of the piston portion may be regulated by the regulation member. After the first application portion applies the primary ejection energy to the substance intended for injection via the piston portion, the regulation member may be broken, such that application of the secondary ejection energy by the second application portion may be performed via the compressed gas.

In the second mode, the compressed gas is in a state of being in contact with the piston portion. However, advancement of the piston portion is regulated by the regulation member. As a result, the energy of the compressed gas is in a state of being accumulated in the filling space. Moreover, the discharged combustion product breaks the regulation member, and this causes the piston portion to be in an advanceable state, in other words, a state where the accumulated energy could be released is established. As a result, the energy of the compressed gas, which is accumulated by being pressed by the compressed gas, is applied, as the secondary ejection energy, to the substance intended for injection via the piston portion. In this application mode, occurrence of exposure of the substance intended for injection to impurities, such as a combustion residue, is suitably prevented.

Next, in a third mode, the above-mentioned injector may further include a piston portion configured to advance in a body of the injector and disposed to be able to apply a pressure to the substance intended for injection that is encapsulated in the encapsulating portion. The energy accumulation portion may include a predetermined space in which an end of the piston portion is exposed, a filling container that is filled with a compressed gas compressed to a predetermined pressure in the inside thereof in a state in which an opening thereof is sealed by a sealing member, and a penetrating member that is disposed to face the sealing member and that enables both inside and outside of the filling container to communicate with each other by penetration through the sealing member. In this case, before application of the primary ejection energy by the first application portion, the compressed gas may be stored in the filling container. When the combustion product is discharged, the first application portion may apply the primary ejection energy to the substance intended for injection via the piston portion and the inside and the outside of the filling container may be made to communicate with each other via the penetrating member by pressing the penetrating member against the sealing member, and then application of the secondary ejection energy by the second application portion may be performed via the compressed gas that is discharged from the filling container.

In the third mode, the energy of the compressed gas is in an accumulated state by being filled in the compressed container. Further, before the primary ejection energy is applied, the compressed gas is not in contact with the piston portion. Note that advancement of the piston portion is not particularly regulated, and is in a state of being advanceable by an external action. Further, the discharged combustion product presses the penetrating member against the sealing member of the filling container, and thus the compressed gas in the filling container can be discharged to the outside of the container, whereby, the energy of the compressed gas is released. As a result, the energy of the compressed gas, which is accumulated by being pressed by the compressed gas, is applied, as the secondary ejection energy, to the substance intended for injection via the piston portion. In this application mode, occurrence of exposure of the substance intended for injection to impurities, such as a combustion residue, is suitably prevented.

Finally, in a fourth mode, the above-mentioned injector may further include a piston portion configured to advance in a body of the injector and disposed to be able to apply a pressure to the substance intended for injection that is encapsulated in the encapsulating portion. The energy accumulation portion may include an elastic member that is in a compressed state and that is disposed in a state of being in contact with the piston portion, and a regulation member configured to regulate advancement of the piston portion to the substance intended for injection. In this case, before the application of the primary ejection energy by the first application portion, advancement of the piston portion may be regulated by the regulation member. After the first application portion applies the primary ejection energy to the substance intended for injection via the piston portion, the regulation member may be broken, such that the application of the secondary ejection energy by the second application portion may be performed by an elongated action of the elastic member.

In the fourth mode, the elastic member in a compressed state is in a state of being in contact with the piston portion. However, advancement of the piston portion is regulated by the regulation member. As a result, s state where an elastic energy of the elastic member is accumulated is established. Moreover, the discharged combustion product breaks the regulation member, and this causes the piston portion to be in an advanceable state, in other words, a state where the accumulated elastic energy could be released is established. As a result, while the elastic member is elongated, the accumulated elastic energy, which is being pressed by the elastic member, is applied, as the secondary ejection energy, to the substance intended for injection via the piston portion. In this application mode, occurrence of exposure of the substance intended for injection to impurities, such as a combustion residue, is suitably prevented.

Advantageous Effects of Invention

With the injector that injects the substance intended for injection to the target region, the substance intended for injection can be caused to suitably reach the target region without affecting the substance intended for injection to be ejected.

DESCRIPTION OF EMBODIMENTS

With reference to the drawings, a needleless injector (hereinafter, simply referred to as "injector") 1, which is one mode of the injector according to the present application, is described below. The injector 1 is a needleless injector that ejects an ejection solution, which corresponds to a substance intended for injection in the present application, to a target region, i.e., a device that injects the injection solution to the target region without an injection needle for injecting the injection solution to the target region. The injector 1 is described below. Note that configurations of the following embodiment are provided as examples, and the invention of the present application is not limited to the configurations of the embodiment. For example, as another mode of the injector according to the present application, an injector including an injection needle may be included.

In this example, "distal end side" and "base end side" are used as terms indicating a relative positional relationship in the longitudinal direction of the injector 1. The "distal end side" indicates a side closer to the distal end of the injector 1 described later, that is, a position closer to an ejection port 45, and the "base end side" indicates a side in an opposite direction to the "distal end side" in a longitudinal direction of the injector 1, that is, a direction to an ignition portion 10 side.

Example 1

Figure 1:
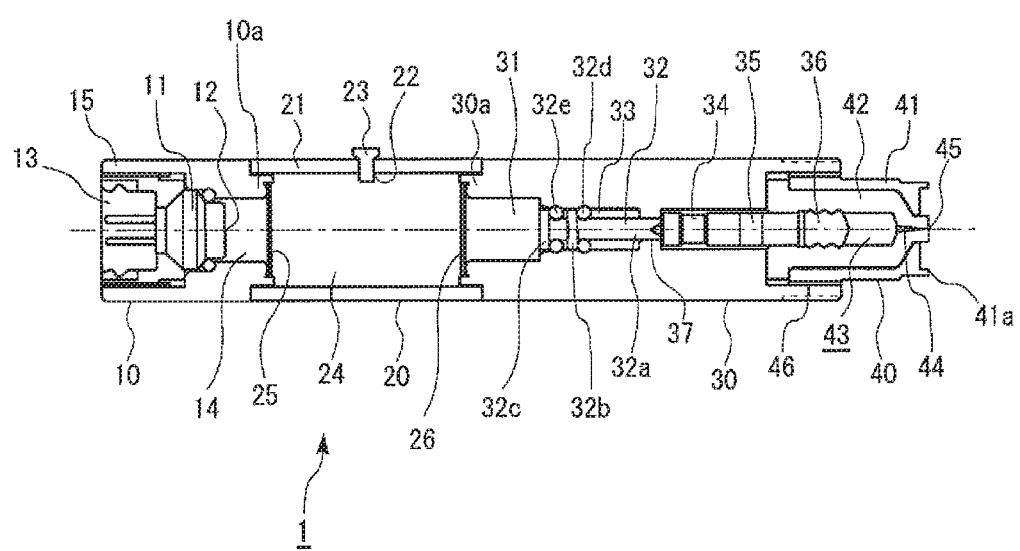
FIG. 1 is a view illustrating a schematic configuration of a first needleless injector according to an embodiment of the present invention.

Here, FIG. 1 is a view illustrating a schematic configuration of the injector 1 in Example 1, and is a cross-sectional view of the injector 1 taken along the longitudinal direction thereof. Note that the injector 1 illustrated in FIG. 1 is in a state before the ignition portion 10 and the like described later are operated. The injector 1 is formed including a syringe portion 40 that is arranged on a distal end side of an injector body 30 and the ignition portion 10 and an accumulation portion 20 that are arranged on a base end side thereof. Note that, in the following description in the present application, an injection solution administered to the target region by the injector 1 is formed containing a liquid medium including a predetermined substance, which exerts an effect or a function expected in the target region. In the injection solution, the predetermined substance may be in a state of being dissolved in liquid, which is a medium, or may be in a state of being simply mixed instead of being dissolved.

For example, examples of the predetermined substance included in the injection solution include an organism-derived substance and a substance having a desired bioactivity, which can be ejected to the target region being an organism. For example, examples of the organism-derived substance include DNA, RNA, a nucleic acid, an antibody, and a cell. Examples of the substance having a desired bioactivity include various substances exerting pharmacological or therapeutic effects, which are exemplified by, low molecule medicine, an inorganic substance such as metal particles for thermotherapy or radiotherapy, and a carrying body functioning as a carrier. Further, it is only required that the liquid, which is the medium of the injection solution, be a substance suitable for administering the above-mentioned predetermined substance exemplified by those substances to the target region, and may be aqueous or oleaginous. Further, viscosity of the liquid, which is the medium, is not particularly limited as long as the predetermined substance can be ejected by the injector 1. Further, the target region, which is an ejection target of the injection solution, is a region to which the above-mentioned predetermined substance is to be administered, and may be exemplified by, for example, a cell or a tissue of an organism (skin or the like), and an organ (an eyeball, a heart, a liver, or the like). Note that, as long as no problem is caused, an organism component in a state of being cut from an organism body can be set as the target region. More specifically, operations of the injector according to the present embodiment include exvivo ejection of the predetermined substance to the target region (a tissue or an organ) and in-vitro ejection of the predetermined substance to the target region (a cultured cell or a cultured tissue).

First, the injector body 30 and the syringe portion 40 are described. A piston portion is arranged inside the injector body 30. The piston portion is pressed by an ejection energy applied from the ignition portion 10 and the accumulation portion 20 described later, and advances in through-holes in the injector body 30 to the distal end side. Specifically, the piston portion includes a drive piston 32 that directly receives the ejection energy and a plunger portion 35 that is pressed by the drive piston 32 and advances. The drive piston 32 mainly advances in a through-hole 33, and the plunger portion 35 mainly advances in a through-hole 34 and an internal portion of the syringe portion 40 described later. The through-hole 33 and the through-hole 34 have substantially the same inner diameter. The through-hole 33 and the through-hole 34 are not directly connected with each other, and are connected through a connecting hole 37 having an inner diameter smaller than those of both the through-holes.

The drive piston 32 is formed of metal, and includes a piston body shaft 32a, a first barrel 32b, and a second barrel 32c. The first barrel 32b and the second barrel 32c have the same outer diameter, but the outer diameter of the piston body shaft 32a is smaller than the outer diameters of the first barrel 32b and the second barrel 32c. The drive piston 32 is arranged in the through-hole 33 such that the first barrel 32h is oriented to the plunger portion 35 side, and the second barrel 32c is oriented to the accumulation portion 20 side. At this time, the second barrel 32c is in a state of being connected to the through-hole 33 and exposed to a side of a predetermined space 31 having an inner diameter larger than that of the through-hole 33. Further, under a state in which the first barrel 32b and the second barrel 32c face an inner surface wall of the through-hole 33 and a state in which the piston body shaft 32a is inserted into the connecting hole 37, the drive piston 32 advances in the through-hole 33 to the distal end side. Further, a coupling portion smaller than the diameter of each of the barrels couples the first barrel 32h and the second barrel 32c with each other, and an O-ring 32e that enhances adhesiveness with the inner wall surface of the through-hole 33 is arranged in a space formed resulting from the coupling between both of the barrels by the coupling portion. Further, an O-ring 32d is arranged also on the distal end side of the first barrel 32h. Note that the drive piston 32 may be formed of a resin, and in such a case, metal may be used additionally for a part to which heat resistance or pressure resistance is required.

Next, the plunger portion 35 and the syringe portion 40 are described. The plunger portion 35 is a member that advances in the through-hole 34 of the injector body 30 by being pressed by the drive piston 32 and applies a pressure to the injection solution filled in a filling chamber 43 by advancing in the filling chamber 43 in the syringe portion 40. Herein, in the syringe portion 40, a syringe body 42, which includes the filling chamber 43, which is a space capable of storing the injection solution, and a nozzle portion 44, which forms a flow path allowing the injection solution to flow therethrough, is screwed together and fixed to the injector body 30 by a holder 41. In FIG. 1, a screwed together position is indicated with the reference numeral 46. Specifically, in the screwed together state, the holder 41 and the injector body 30 sandwich and fix the syringe body 42 therebetween, and the center axis of the filling chamber 43 provided to extend in the longitudinal direction of the syringe body 42 matches with the center axis of the through-hole 34 in the extending direction. With this configuration, the plunger portion 35 is capable of smoothly advancing in the through-hole 34 and the filling chamber 43. Further, on the distal end side of the nozzle portion 44, the ejection port 45 for ejecting the injection solution to the outside of the injector 1 is formed.

Here, known nylon 6-12, polyarylate, polybutylene terephthalate, polyphenylene sulphide, a liquid crystal polymer, or the like may be used for the syringe body 42. Further, a filler such as glass fibers and glass filler may be contained in those resins. 20 to 80 mass % of glass fibers may be contained in polybutylene terephthalate, 20 to 80 mass % of glass fibers may be contained in polyphenylene sulphide, or 20 to 80 mass % of minerals may be contained in a liquid crystal polymer.

Further, in the filling chamber 43 formed in an internal portion of the syringe portion 40, a space formed between a pressing portion 36 and the syringe body 42 that are provided on the distal end side of the plunger portion 35 serves as a space in which the injection solution is encapsulated. Further, as the plunger portion 35 advances in the filling chamber 43 the injection solution stored in the filling chamber 43 is pressed and ejected through the ejection port 45 provided on the distal end side of the nozzle portion 44. Thus, the pressing portion 36 is formed of a material that allows smooth advancement in the filling chamber 43 and prevents the injection solution from leaking from the plunger portion 35 side. Specific examples of materials of the pressing portion 36 include butyl rubber and silicon rubber. Further, the material may be exemplified a styrene-based elastomer or a hydrogenated styrene-based elastomer, or a substance obtained by mixing a styrene-based elastomer or a hydrogenated styrene-based elastomer with polyolefin such as polyethylene, polypropylene, polybutene, and an α-olefin copolymer, oil such as liquid paraffin and process oil, or a powder inorganic substance such as talc, cast, and mica. Further, as the material of the pressing portion 36, a polyvinyl chloride-based elastomer, an olefin-based elastomer, a polyester-based elastomer, a polyamide-based elastomer, a polyurethane-based elastomer, various rubber materials (particularly, a vulcanized material) such as natural rubber, isoprene rubber, chloroprene rubber, nitrile butadiene rubber, and styrene butadiene rubber, or a mixture thereof may be employed. Moreover, for the purpose of securing and adjusting advance between the pressing portion 36 and the syringe body 42, the surface of the pressing portion 36 and the surface of the filling chamber 43 of the syringe body 42 may be subjected to coating or surface finishing with various substances. Examples of coating agents may include polytetrafluoroethylene (PTFE), silicon oil, diamond-like carbon, nanodiamond, and the like.

Here, the outline of the pressing portion 36 on the distal end side has a shape that substantially matches with the outline of an inner wall surface of the filling chamber 43 on the distal end side. With this, when the plunger portion 35 advances in the filling chamber 43 and arrives at the deepest position located deepest in the filling chamber 43 at the time of ejection of the injection solution, a gap formed between the pressing portion 36 and the inner wall surface of the filling chamber 43 can be reduced as small as possible, and the injection solution can be prevented from remaining in the filling chamber 43 and being wasted. However, the shapes of the plunger portion 35 and the pressing portion 36 are not particularly limited to a specified shape as long as a desired effect can be obtained with the injector according to the present embodiment.

Here, description returns to the syringe portion 40. The inner diameter of the flow path provided in the nozzle portion 44 of the syringe body 42 is formed to be smaller than the inner diameter of the filling chamber 43. With this configuration, the injection solution that has been applied with a high pressure is ejected to the outside through the ejection port 45 of the flow path. In view of this, on the distal end side of the holder 41 forming the syringe portion 40 and in the vicinity of the ejection port 45 of the nozzle portion 44, an annular shield portion 41a is provided to surround the periphery of the ejection port 45. For example, when the ejection port 45 is pressed against the target region such as a surface of human skin and the injection solution is ejected, the shield portion 41a can perform shielding to prevent the ejected injection solution from scattering in the periphery. Note that the skin is pushed down to a certain extent when the ejection port 45 is pressed against the skin, and this can enhance contact between the ejection port 45 and the skin and prevent the injection solution from scattering. In view of this, the distal end of the nozzle portion 44, at which the ejection port 45 is positioned, may be at a height substantially flush with the end surface of the shield portion 41a, or the distal end of the nozzle portion 44 may slightly protrude from the end surface of the shield portion 41a in the ejection direction of the injection solution.

Next, a configuration of the injector 1 is described, in which ejection energy is applied to the injection solution such that the injection solution encapsulated in the syringe portion 40 is ejected to the target region through the ejection port 45. In this example, the ignition portion 10 and the accumulation portion 20 apply the ejection energy.

First, the ignition portion 10 is described. The ignition portion 10 includes an ignition portion body 15 which is formed in a tubular shape and which includes an igniter 11 and a power source portion 13. The igniter 11 is an electric igniter that combusts ignition charge, discharges a combustion product, and generates an ejection energy for ejecting the injection solution; and the power source portion 13 supplies the igniter 11 with an ignition current for the ignition charge. Further, an operation button used by a user to supply the ignition current is arranged in the power source portion 13. The combustion product generated by the igniter 11 is discharged to a discharge space 14 from a discharge surface 12 facing the accumulation portion 20 in the igniter 11. Note that the igniter 11 may be attached to the ignition portion body 15 via a member in which an injection molded resin is fixed to a metal collar. The injection molding may be performed by a known method. Further, resin material same as that of the syringe body 42 may be employed as a resin material to be used for the injection molding.

Here, a combustion energy for the ignition charge used in the igniter 11 is an energy by which the injector 1 ejects the injection solution to the target region. Note that examples of the ignition charge include an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), an explosive containing aluminum and iron oxide (AFO), or an explosive composed of a combination of a plurality of the explosives thereof. These explosives exhibit characteristics in which, although the explosives generate high-temperature and high-pressure plasma during combustion immediately after ignition, when, at room temperature, the combustion product condenses, the explosives contain no gaseous component and hence the pressure generated decreases abruptly. An explosive other than these may be used as the ignition charge as long as appropriate ejection of the injection solution can be performed.

The accumulation portion 20 is described below. The accumulation portion 20 is arranged between the ignition portion 10 and the injector body 30. The accumulation portion 20 includes a tubular accumulation portion body 21 and two metal plate members 25 and 26. With this configuration, a filling space 24 that can be filled with compressed gas is defined inside the accumulation portion 20. The plate member 25 is arranged on the discharge space 14 side of the ignition portion 10 to face the discharge surface 12 of the igniter 11. Specifically, the plate member 25 is fixed to be fitted into a step portion 10a provided at an end (an end on the distal end side) of the ignition portion body 15 of the ignition portion 10. The fixing is implemented to the ignition portion body 15 by a suitable method, such as welding, such that airtightness of the filling space 24 is kept. Further, the plate member 26 is arranged on the predetermined space 31 side of the injector body 30 to face the second barrel 32c of the drive piston 32. Specifically, the plate member 26 is fixed to be fitted into a step portion 30a provided at an end (an end on the base end side) of the injector body 30. The fixing is implemented to the injector body 30 by a suitable method, such as welding, such that airtightness of the filling space 24 is kept.

Here, the compressed gas filled in the filling space 24 is inert gas, such as argon gas, helium gas, nitrogen gas, and carbon dioxide gas. The compressed gas, which is filled, is gas that may come into contact with the combustion product discharged by the operation of the igniter 11 as described later, hence the above-mentioned gas is used for the purpose of preventing an unnecessary chemical reaction to be caused by such contact. Note that, the unnecessary chemical reaction described herein indicates a chemical reaction that generates impurities such as a combustion residue and fine particles, hence as long as impurities are not generated, compressed gas other than inert gas may be used. Further, filling the filling space 24 with the compressed gas is performed through a through-hole 22 for filling, which is provided in the accumulation portion body 21. After implementing filling of the compressed gas through the through-hole 22, the through-hole 22 is closed with a closing pin 23 such that the compressed gas is prevented from leaking.

Here, the plate members 25 and 26 have a thickness capable of exerting strength that withstands a pressure of the compressed gas filled in the filling space 24 before the operation of the igniter 11 and that may cause breakage by the combustion product discharged from the discharge surface 12 of the igniter 11. Therefore, before the operation of the igniter 11, a state is formed in the accumulation portion 20 where an energy of the compressed gas is accumulated, with the compressed gas being stored in the filling space 24. Moreover, when the igniter 11 is operated, the combustion product, which has been discharged, breaks the plate members 25 and 26, and the compressed gas, which has been filled, is released to the outside of the filling space 24. In view of this point, application of the ejection energy to the injection solution in the injector 1 is described below.

Before the igniter 11 is operated, the compressed gas is stored in the filling space 24 as described above. Thus, a state where the plate member 26 prevents contact between the compressed gas and the drive piston 32 is kept, hence no ejection energy is applied to the injection solution via the drive piston 32 and the plunger portion 35. Further, when the igniter 11 is operated, the combustion product is discharged from the discharge surface 12 to the plate member 25. As a result, the plate member 25 and the plate member 26, which are positioned ahead in the discharge direction, are broken by the discharged combustion product.

Here, a combustion speed of the ignition charge of the igniter 11 is relatively high, and a discharge speed of the combustion product is higher than a speed at which the compressed gas which has been filled, is discharged from the filling space 24. Thus, the combustion product first acts on the second barrel 32c of the drive piston 32, whereby the energy of the combustion product is applied, as the ejection energy, to the injection solution via the drive piston 32. With this, the drive piston 32 advances, and ejection of the injection solution starts. The ejection energy that is applied after being generated mainly due to the combustion product corresponds to a primary ejection energy in the present application. Moreover, after that, the compressed gas filled in the filling space 24 flows through a breakage part of the broken plate member 26, and comes into contact with the second barrel 32c of the drive piston 32. Then, the energy of the compressed gas is additionally applied, as the ejection energy, to the injection solution via the drive piston 32. With this, the drive piston 32 further advances, whereby ejection of the injection solution is facilitated. The ejection energy that is applied after being generated mainly due to the compressed gas corresponds to a secondary ejection energy in the present application.

Figure 2:
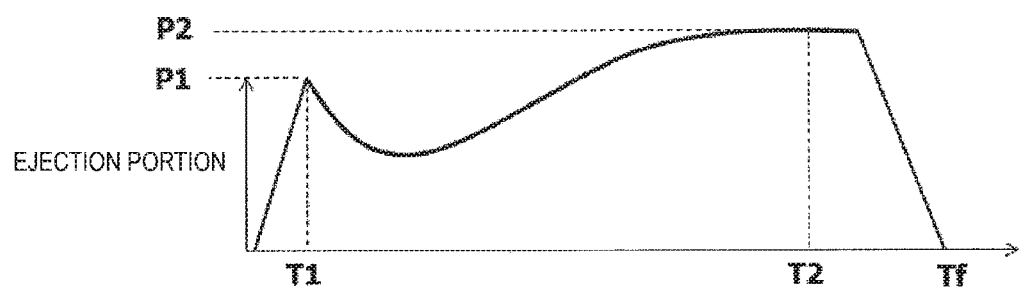
FIG. 2 is a view illustrating transition of an ejection pressure of an injection solution ejected by the needleless injector illustrated in FIG. 1.

FIG. 2 shows transition of a pressure (hereinafter, simply referred to as "ejection pressure") of the injection solution ejected from the ejection port 45 at the time of applying the primary ejection energy and the secondary ejection energy to the injection solution as described above. In FIG. 2, a horizontal axis indicates elapsed time, and a vertical axis indicates an ejection pressure. Note that the ejection pressure can be measured using a technique in the related art. For example, similarly to the measurement method described in JP 2005-21640 A, an ejection force may be measured by a method in which a force of ejection is applied in a dispersed manner to a diaphragm of a load cell arranged downstream of the nozzle, and output from the load cell is collected by a data collection device via a detection amplifier to be stored as an ejection force (N) for every hour. The ejection force measured in this manner is divided by an area of the ejection port 45 of the injector 1, whereby the ejection pressure is calculated.

The ejection pressure transition shown in FIG. 2 is transition of the ejection pressure from the start of combustion to a time at which the ejection pressure becomes approximately zero, with the time, at which the operation button is pressed in the ignition portion 10, being a starting time point. During the transition of the ejection pressure, two peak pressures P1 and P2 emerge. Herein, the peak pressure P1 is referred to as a first peak pressure, and a timing at which the first peak pressure P1 emerges is referred to as a first timing T1. Moreover, the peak pressure P2 is referred to as a second peak pressure, and a timing at which the second peak pressure P2 emerges is referred to as a second timing T2. Further, a timing at which the ejection pressure becomes approximately zero is indicated with Tf. Note that, in this example, a time period from a time at which the combustion product acts on the drive piston 32 to a time at which the compressed gas acts on the drive piston 32 is relatively short. Thus, a period from the first timing T1 to the second timing T2 may be relatively short. Hence, in some cases, after reaching the first peak pressure P1, the ejection pressure may not be lowered greatly before reaching the second peak pressure P2.

Here, the first peak pressure P1 is mainly considered as a value of a pressure generated from the combustion product that first acts on the drive piston 32. The injection solution under the ejection pressure of the first peak pressure P1 is an injection solution that is to be ejected from the injector 1 at an early stage, and penetrates the surface of the target region. Further, after that, the ejection pressure of the injection solution is lowered to a pressure lower than the first peak pressure, and then is raised again to the second peak pressure P2. The second peak pressure P2 is mainly considered as a value of a pressure generated by the released compressed gas that acts, secondary to the combustion product, on the drive piston 32. The injection solution under the ejection pressure of the second peak pressure P2 is most of the injection solution to be delivered into the target region. When the second peak pressure P2 is generated by releasing the compressed gas filled in the filling space 24 as in this example, although it depends on a filling amount of the compressed gas (a gas pressure), the ejection pressure can be maintained at a relatively high pressure value which is close to the second peak pressure P2 for a relatively long time period. Thus, a relatively large amount of the injection solution can be delivered into the target region.

Moreover, in this example, after the primary ejection energy generated by the combustion product is applied to the injection solution, contact between the released compressed gas and the drive piston 32 applies the secondary ejection energy to the injection solution. In this application mode, the combustion product breaks substantially only the plate members 25 and 26, and a chemical reaction that generates impurities does not occur at the time of releasing the energy of the compressed gas. Thus, the injection solution is suitably prevented from being exposed to impurities. Further, a gas temperature is lowered along with the gas pressure when the compressed gas is discharged from the filling space 24, hence the combustion product can be cooled effectively.

Example 2

Figure 3:
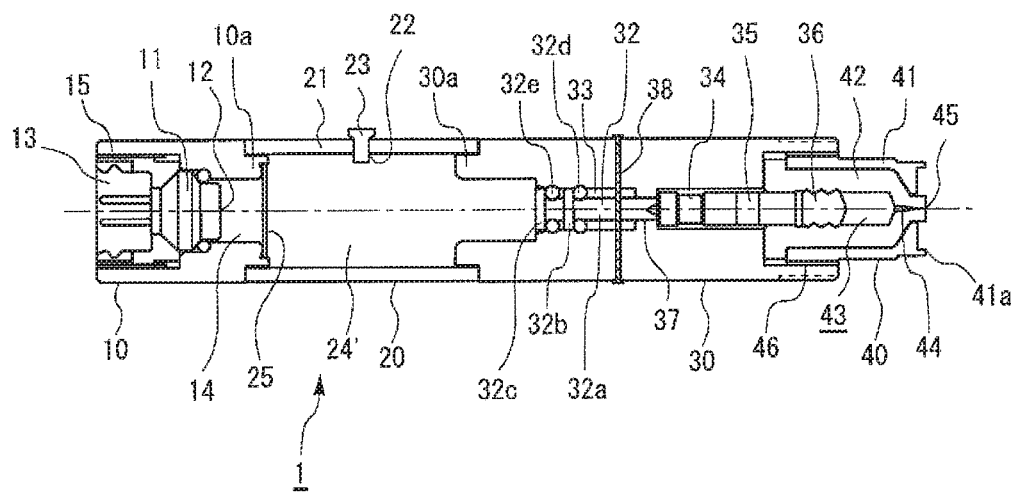
FIG. 3 is a view illustrating a schematic configuration of a second needleless injector according to an embodiment of the present invention.

The injector 1 according to Example 2 is described with reference to FIG. 3. The injector 1 illustrated in FIG. 3 is in a state before the ignition portion 10 and the like are operated. Note that, among the configurations of the injector 1 illustrated in FIG. 3 in this example, detailed description on the configurations that are substantially the same as those of the injector 1 illustrated in FIG. 1, is omitted by denoting the same reference numerals. The injector 1 illustrated in FIG. 3 in this example and the injector 1 illustrated in FIG. 1 are different from each other mainly in the configuration of the accumulation portion 20. In this example, the accumulation portion 20 includes the tubular accumulation portion body 21, the metal plate member 25, and a metal shear pin 38. The accumulation portion body 21, the plate member 25, and the second barrel 32c of the drive piston 32 (the O-ring 32e) define a filling space 24' that can be filled with the compressed gas inside the accumulation portion 20. The filling space 24' substantially corresponds to a space obtained by combining the filling space 24 and the predetermined space 31 in Example 1. The compressed gas filled in the filling space 24' is the same that in the case of Example 1. Therefore, the compressed gas filled in the filling space 24' is in a state of being in contact with the second barrel 32c of the drive piston 32.

Here, the shear pin 38 is a member that regulates advancement of the drive piston 32 in the through-hole 33. Specifically, the shear pin 38 passes through a through-hole provided in the piston body shaft 32a of the drive piston 32, and is fixed to the injector body 30. In this manner, the shear pin 38 regulates advancement of the drive piston 32. However, the shear pin 38 has strength that can withstand a pressure of the compressed gas filled in the filling space 24' and prevent advancement of the drive piston 32 before the operation of the igniter 11 and strength that cause breakage by the combustion product discharged when the igniter 11 is operated. Therefore, before the operation of the igniter 11, in the accumulation portion 20, a state is formed in which an energy of the compressed gas is accumulated, with the compressed gas being stored in the filling space 24'. Further, when the igniter 11 is operated, the discharged combustion product breaks the plate member 25 and the shear pin 38, whereby a state in which the filled compressed gas acts on the drive piston 32 to cause the same to be able to advance. In view of this point, application of the ejection energy to the injection solution in the injector 1 is described below.

Before the igniter 11 is operated, the compressed gas is stored in the filling space 24' as described above. At this time, the compressed gas is in contact with the drive piston 32, but advancement of the drive piston 32 is regulated by the shear pin 38. Thus, no ejection energy is applied to the injection solution via the drive piston 32 and the plunger portion 35. Further, when the igniter 11 is operated, the combustion product is discharged from the discharge surface 12 to the plate member 25. As a result, the plate member 25, which is positioned ahead in the discharge direction, is broken. Further, the discharged combustion product acts on the second barrel 32c of the drive piston 32. At this time, in a microscopic view, the energy of the combustion product plastically deforms the shear pin, and the drive piston 32 advances by a slight amount. That is, the energy of the combustion product is applied, as the ejection energy, to the injection solution via the drive piston 32. With this, ejection of the injection solution starts. The ejection energy that is applied after being generated mainly due to the combustion product corresponds to a primary ejection energy in the present application.

Further, after that, the energy of the combustion product breaks the shear pin 38, whereby the regulated state of the drive piston 32 by the shear pin 38 is canceled. As a result, the energy of the compressed gas held in contact with the drive piston 32 is additionally applied, as the ejection energy, to the injection solution via the drive piston 32. With this, the drive piston 32 further advances, whereby ejection of the injection solution is facilitated. The ejection energy that is applied after being generated mainly due to the compressed gas after breakage of the shear pin 38 corresponds to the secondary ejection energy in the present application.

As described above, after the primary ejection energy generated by the combustion product is applied to the injection solution, the compressed gas applies the secondary ejection energy to the injection solution. As a result, as shown in FIG. 2, the ejection pressure of the injection solution ejected from the ejection port 45 transitions to a higher pressure, i.e., the first peak pressure P1 at the first timing T1 generated mainly due to the combustion product. After that, the ejection pressure is lowered to a pressure lower than the first peak pressure, and the ejection pressure is raised again to the second peak pressure P2 generated mainly due to the compressed gas. As a result, the injection solution can be delivered into the target region suitably. Further, as the compressed gas is used, the ejection pressure can be maintained at a relatively high pressure value which is close to the second peak pressure P2 for a relatively long time period during the ejection pressure transition, by adjusting the filling amount (the gas pressure) of the compressed gas in the filling space 24'. Thus, a relatively large amount of the injection solution can be delivered into the target region.

Further, in the mode of applying the ejection energy in this example, substantially, the combustion product breaks only the plate member 25 and the shear pin 38, and a chemical reaction that generates impurities is not caused at the time of releasing the energy of the compressed gas. Thus, the injection solution is suitably prevented from being exposed to impurities.

Modified Example 1

Figure 4:
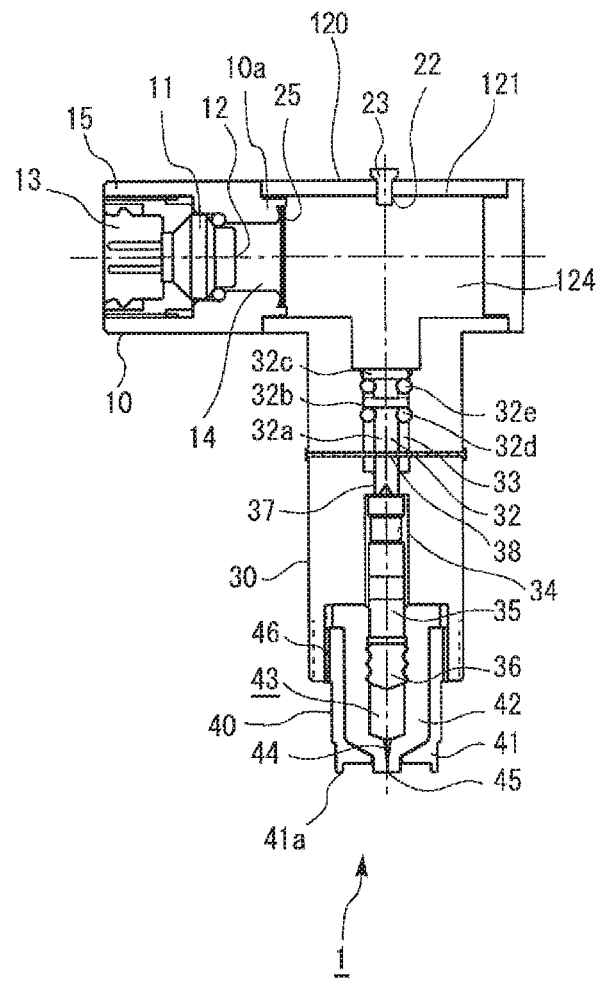
FIG. 4 is a view illustrating a schematic configuration of a third needleless injector according to an embodiment of the present invention.

Here, Modified Example 1 of this example is illustrated in FIG. 4. The injector 1 illustrated in FIG. 4 is in a state before the ignition portion 10 and the like are operated. Note that, among the configurations of the injector 1 illustrated in FIG. 4 in this example, detailed description on the configurations that are substantially the same as those of the injector 1 illustrated in FIG. 3, is omitted by denoting the same reference numerals. The injector 1 illustrated in FIG. 4 in this example and the injector 1 illustrated in FIG. 3 are different from each other in a configuration of an accumulation portion 120.

The accumulation portion 120 in this modified example is arranged between the ignition portion 10 and the injector body 30. The injector body 30 is attached to an accumulation portion body 121 such that the center axis of the ignition portion 10 in the longitudinal direction and the center axis of the injector body 30 and the syringe portion 40 in the longitudinal direction are orthogonal to each other. Further, the compressed gas is filled in a filling space 124 formed inside the accumulation portion body 121. The compressed gas is in contact with the second barrel 32c of the drive piston 32. However, similarly to Example described above, the shear pin 38 regulates advancement of the drive piston 32.

Similarly to Example described above, also with the injector 1 configured in this way, the injection solution can be suitably prevented from being exposed to impurities. Moreover, the center axis of the ignition portion 10 in the longitudinal direction and the center axis of the injector body 30 in the longitudinal direction are orthogonal to each other, and hence a total length of the injector 1 can be reduced.

Modified Example 2

Figure 5:
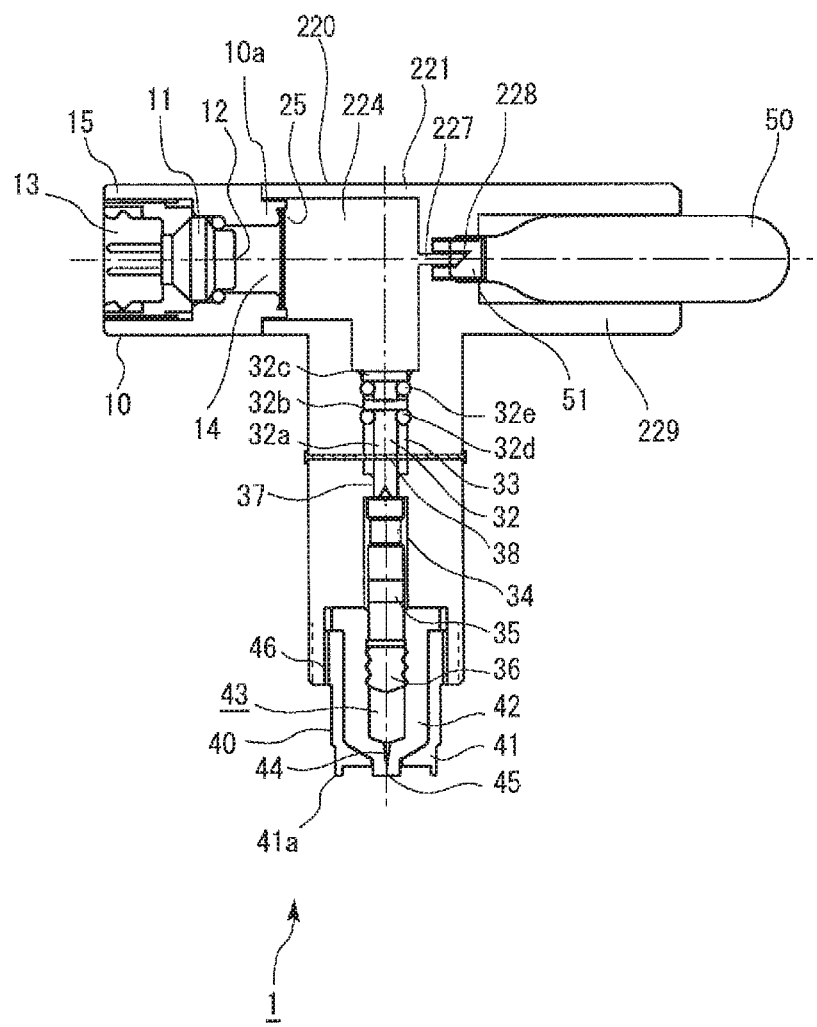
FIG. 5 is a view illustrating a schematic configuration of a fourth needleless injector according to an embodiment of the present invention.

Here, Modified Example 2 in this example is illustrated in FIG. 5. The injector 1 illustrated in FIG. 5 is in a state before the ignition portion 10 and the like are operated. Note that, among the configurations of the injector 1 illustrated in FIG. 5 in this example, detailed description on the configurations that are substantially the same as those of the injector 1 illustrated in FIG. 4, is omitted by denoting the same reference numerals. The injector 1 illustrated in FIG. 5 in this modified example includes the injector body 30 and the accumulation portion 120 illustrated in FIG. 4 in an integrated manner, and this integrated configuration is referred to as an accumulation portion 220. That is, the accumulation portion 220 has also a configuration that has functions of the injector body described above.

Similarly to Modified Example 1 described above, also in the injector 1 in this modified example, the accumulation portion 220 is attached to the ignition portion 10 and the syringe portion 40 such that the center axis of the ignition portion 10 in the longitudinal direction and the center axis of the syringe portion 40 in the longitudinal direction are orthogonal to each other. Here, the accumulation portion 220 includes an accumulation portion body 221, the plate member 25, and a filling container attachment portion 229. The filling container attachment portion 229 is a part for attaching a filling container 50 filled with the compressed gas to the injector 1. The filling container 50 has an opening that is sealed with a sealing member 51, and thus the inside thereof is filled with the compressed gas. Further, when the filling container 50 is attached to the filling container attachment portion 229, the sealing member of the filling container 50 pierces a penetrating member 228 provided at an end of a filling path 227 communicating with a filling space 224 formed inside the accumulation portion body 221, whereby a through-hole is formed at the pierced position. Then, the compressed gas in the filling container 50 moves to the filling space 224 side, thereby filling the filling space 224 with the compressed gas. Further, the compressed gas is in contact with the second barrel 32c of the drive piston 32. However, similarly to Example described above, the shear pin 38 regulates advancement of the drive piston 32.

Similarly to Example described above, also with the injector 1 configured in this way, the injection solution can be suitably prevented from being exposed to impurities. Moreover, the injector 1 has a configuration such that the compressed gas can be filled in the filling space 224, by attaching the filling container 50 to the injector 1. With this, it becomes easier to carry the injector 1 together with the filling container 50, and convenience of the injector 1 can be enhanced.

Example 3

Figure 6:
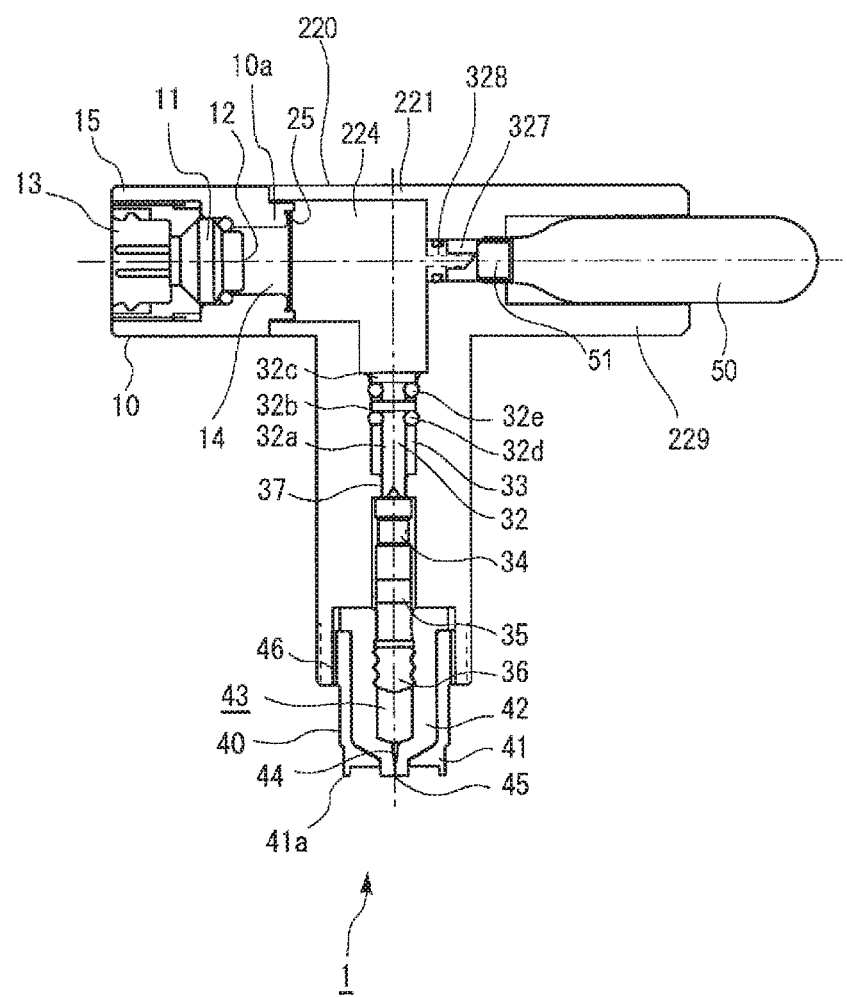
FIG. 6 is a view illustrating a schematic configuration of a fifth needleless injector according to an embodiment of the present invention.

The injector 1 according to Example 3 is described with reference to FIG. 6. The injector 1 illustrated in FIG. 6 is in a state before the ignition portion 10 and the like are operated. Note that, among the configurations of the injector 1 illustrated in FIG. 6 in this example, detailed description on the configurations that are substantially the same as those of the injector 1 illustrated in FIG. 5, is omitted by denoting the same reference numerals. The injector 1 illustrated in FIG. 6 in this example and the injector 1 illustrated in FIG. 5 are different from each other in the configuration of moving the compressed gas from the filling container 50 to the filling space, and presence or absence of the shear pin 38 in the accumulation portion 220.

In this example, when the filling container 50 is attached to the filling container attachment portion 229, the opening of the filling container 50 is inserted into a filling path 327 communicating with the filling space 224, and the sealing member 51 is in a state of facing a penetrating member 328 arranged in the filling path 327. The penetrating member 328 is arranged movably inside the filling path 327, and includes a predetermined seal member to enhance contact between the penetrating member 328 and an inner wall surface of the filling path 327. Further, the penetrating member 328 is formed in a sharp shape on the distal end side thereof facing the sealing member 51. Inside thereof, a through-hole that makes the distal end side of the penetrating member 328 and the filling space 224 side communicate with each other is formed. Therefore, when the penetrating member 328 sufficiently pierces the sealing member 51, the through-hole inside thereof enables the compressed gas in the filling container 50 to move to the filling space 224 side. Note that, in the state before the igniter 11 is operated in FIG. 6, the penetrating member 328 does not pierce the sealing member 51 yet, hence the compressed gas is not present in the filling space 224. Therefore, without a member, such as the shear pin 38, that regulates advancement of the drive piston 32, the drive piston 32 does not advance. As described above, before the igniter 11 is operated, the accumulation portion 220 accumulates the energy of the compressed gas, with the compressed gas being stored in the filling container 50. Moreover, when the igniter 11 is operated, the penetrating member 328 pierces the sealing member 51 by being pressed by the discharged combustion product. As a result, the compressed gas in the filling container 50 moves to the filling space 224, thereby enabling the drive piston 32 to advance. In view of this point, application of the ejection energy to the injection solution in the injector 1 is described below.

Before the igniter 11 is operated, the compressed gas is stored in the filling container 50 as described above. Thus, no ejection energy is applied to the injection solution via the drive piston 32 and the plunger portion 35. Moreover, when the igniter 11 is operated, the combustion product is discharged from the discharge surface 12 to the plate member 25. As a result, the plate member 25, which is positioned ahead in the discharge direction, is broken. Further, the discharged combustion product acts on the second barrel 32c of the drive piston 32, whereby the drive piston 32 advances. That is, the energy of the combustion product is applied, as the ejection energy, to the injection solution via the drive piston 32. With this, ejection of the injection solution starts. The ejection energy that is applied after being generated mainly due to the combustion product corresponds to a primary ejection energy in the present application.

Moreover, when the energy of the combustion product causes the penetrating member 328 to move in the filling path 327 and pierce the sealing member 51, the compressed gas in the filling container 50 is discharged to the filling space 224 through the through-hole of the penetrating member 328, and comes into contact with the second barrel 32c of the drive piston 32. As a result, the energy of the compressed gas is additionally applied, as the ejection energy, to the injection solution via the drive piston 32. With this, the drive piston 32 further advances, thereby facilitating ejection of the injection solution. The ejection energy that is applied after being generated mainly due to the compressed gas, after the compressed gas is discharged from the filling container 50, corresponds to a secondary ejection energy in the present application.

As described above, after the primary ejection energy generated by the combustion product is applied to the injection solution, the compressed gas applies the secondary ejection energy to the injection solution. As a result, as shown in FIG. 2, the ejection pressure of the injection solution ejected from the ejection port 45 transitions to a higher pressure, i.e., the first peak pressure P1 at the first timing T1 generated mainly due to the combustion product. After that, the ejection pressure is lowered to a pressure lower than the first peak pressure, and the ejection pressure is raised again to the second peak pressure P2 generated mainly due to the compressed gas. As a result, the injection solution can be delivered into the target region suitably. Further, as the compressed gas is used the ejection pressure can be maintained at a relatively high pressure value which is close to the second peak pressure P2 for a relatively long time period during the ejection pressure transition, by adjusting the filling amount (the gas pressure) of the compressed gas in the filling container 50. Thus, a relatively large amount of the injection solution can be delivered into the target region.

Further, in the mode of applying the ejection energy in this example, substantially, the combustion product only breaks the plate member 25 and presses the penetrating member 328 against the sealing member 51, and a chemical reaction that generates impurities is not caused at the time of releasing the energy of the compressed gas. Thus, the injection solution is suitably prevented from being exposed to impurities.

Example 4

Figure 7:
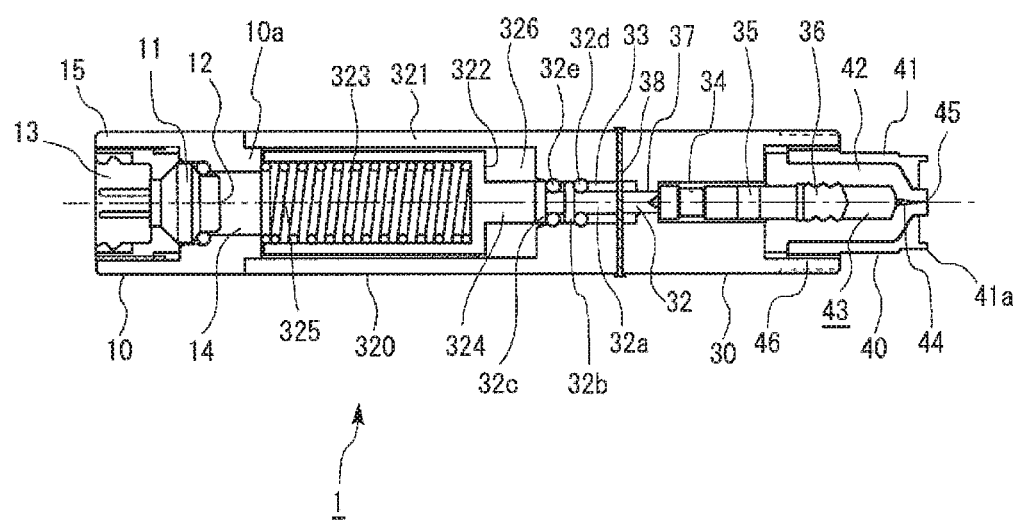
FIG. 7 is a view illustrating a schematic configuration of a sixth needleless injector according to an embodiment of the present invention.

The injector 1 according to Example 4 is described with reference to FIG. 7. The injector 1 illustrated in FIG. 7 is in a state before the ignition portion 10 and the like are operated. Note that, among the configurations of the injector 1 illustrated in FIG. 7 in this example, detailed description on the configurations that are substantially the same as those of the injector 1 illustrated in FIG. 3, is omitted by denoting the same reference numerals. The injector 1 illustrated in FIG. 7 in this modified example includes the injector body 30 and the accumulation portion 20 illustrated in FIG. 3 in an integrated manner, and this integrated configuration is referred to as an accumulation portion 320. That is, the accumulation portion 320 has also a configuration having functions of the injector body 30 described above.

The injector 1 illustrated in FIG. 7 in this example and the injector 3 illustrated in FIG. 1 are different from each other mainly in the configuration of the accumulation portion 320. In this example, the accumulation portion 320 accumulates a compressed energy of an elastic member, and specifically includes an accumulation portion body 321, a spring holder 322, a spring 325, and the metal shear pin 38. The spring holder 322 includes an accommodation space 323 that accommodates the spring 325 and a neck portion 324 having an outer diameter having a size substantially the same as that of the inner diameter of the through-hole 33, and is arranged in an internal space 326 of the accumulation portion body 321 such that an opening of the accommodation space 323 is positioned on the ignition portion 10 side and the neck portion 324 is positioned on the drive piston 32 side. The internal space 326 is a space communicating with the through-hole 33. Further, in the state illustrated in FIG. 7, one end of the spring 325 is in contact with the ignition portion body 15, and the other end thereof is in contact with a bottom of the accommodation space 323. With this, the spring 325 is in a compressed state. Moreover, the neck portion 324 of the spring holder 322 is in contact with the second barrel 32c of the drive piston 32. Note that, in this state, advancement of the drive piston 32 is regulated by the shear pin 38. Thus, before the igniter 11 is operated, the accumulation portion 320 is in a state of accumulating an elastic energy of the compressed spring 325. Further, when the igniter 11 is operated, the discharged combustion product breaks the shear pin 38, and the compressed spring 325 acts on the drive piston 32 and causes the same to advance. In view of this point, application of the ejection energy to the injection solution in the injector 1 is described below.

Before the igniter 11 is operated, the neck portion 324 of the spring holder 322 that accommodates the compressed spring 325 is in contact with the drive piston 32, but advancement of the drive piston 32 is in a state of being regulated by the shear pin 38. Thus, no ejection energy is applied to the injection solution via the drive piston 32 and the plunger portion 35. Moreover, when the igniter 11 is operated, the combustion product is discharged from the discharge surface 12 to the spring 325. As a result, the discharged combustion product acts on the second barrel 32c of the drive piston 32 via the spring holder 322. At this time, in a microscopic view, the energy of the combustion product plastically deforms the shear pin 38, whereby the drive piston 32 advances by a slight amount. That is, the energy of the combustion product is applied, as the ejection energy, to the injection solution via the drive piston 32. With this, ejection of the injection solution starts. The ejection energy that is applied after being generated mainly due to the combustion product corresponds to a primary ejection energy in the present application.

Moreover, after that, the energy of the combustion product breaks the shear pin 38, whereby the regulation state of the drive piston 32 by the shear pin 38 is canceled. As a result, the elastic energy of the compressed spring 325 held in contact with the drive piston 32 is additionally applied, as the ejection energy, to the injection solution via the drive piston 32. With this, the drive piston 32 further advances, thereby facilitating ejection of the injection solution. The ejection energy that is applied after being generated mainly due to the spring 325 after breakage of the shear pin 38 corresponds to the secondary ejection energy in the present application.

As described above, after the primary ejection energy generated by the combustion product is applied to the injection solution, the compressed spring 325 applies the secondary ejection energy to the injection solution. As a result, as shown in FIG. 2, the ejection pressure of the injection solution ejected from the ejection port 45 transitions to a higher pressure, i.e., the first peak pressure P1 at the first timing T1 that is mainly generated due to the combustion product. After that, the ejection pressure is lowered to a pressure lower than the first peak pressure, and the ejection pressure is raised again to the second peak pressure P2 that is mainly generated by the spring 325. As a result, the injection solution can be delivered into the target region suitably.

Further, in the mode of applying the ejection energy in this example, substantially, the combustion product only breaks the shear pin 38, and a chemical reaction that generates impurities is not caused at the time of releasing the elastic energy of the compressed spring 325. Thus, the injection solution is suitably prevented from being exposed to impurities.

Other Modified Examples

As a further modified example of the injector 1, for example, a device can be exemplified that performs inoculation with a cultured cell, a stem cell, or the like into a cell, a scaffold tissue, or a scaffold, i.e., an injection target, in a field of regenerative medicine for a human. For example, as described in JP 2008-206477 A, in accordance with an implanted part and a purpose of re-cellularization, a cell that can be determined appropriately by a person skilled in the art, for example, an endothelial cell, an endothelial precursor cell, a myeloid cell, a preosteoblast cell, a cartilagenous cell, a fibroblast cell, a skin cell, a muscle cell, a liver cell, a kidney cell, an intestinal cell, a stem cell, or any other cells that may be considered in the field of regenerative medicine is administered.

Moreover, the injector 1 may be configured as an injector that delivers DNA or the like into a cell, a scaffold tissue, a scaffold, or the like as described in JP 2007-525192 T. Moreover, the injector 1 may be configured as an injector that directly delivers various genes, a cancer-suppressing cell, a lipid envelope, or the like into a target tissue or administrates an antigenic gene for enhancing immunity against a pathogen, or an injector applicable in a field of treatment for various diseases (the fields described in JP 2008-508881 T, JP 2010-503616 T, and the like), a field of immunological medicine (the field described in JP 2005-523679 T and the like), and the like.

REFERENCE SIGNS LIST

1 Injector
10 Ignition portion
11 Igniter
15 Ignition portion body
20, 120, 220, 320 Accumulation portion
21, 121, 221, 321 Accumulation portion body
24, 24', 124, 224 Filling space
25, 26 Plate member
30 Injector body
32 Drive piston
32c Second barrel
33 Through-hole
34 Through-hole
35 Plunger portion
36 Pressing portion
38 Shear pin
40 Syringe portion
41 Holder
41a Shield portion
42 Syringe body
43 Filling chamber
44 Nozzle portion
45 Ejection port
50 Filling container
51 Sealing member
227 Filling path
228 Penetrating member
229 Filling container attachment portion
322 Spring holder
323 Accommodation space
324 Neck portion
325 Spring
326 Internal space
327 Filling path
328 Penetrating member

What is claimed is:

1. An injector injecting a substance intended for injection to a target region, the injector comprising:
  an encapsulating portion configured to encapsulate the substance intended for injection;
  a piston portion configured to advance in a body of the injector and disposed to apply a pressure to the substance encapsulated in the encapsulating portion so as to inject the substance to the target region;
  an igniter configured to combust an ignition charge and discharge a combustion product as a primary ejection energy; and
  an energy accumulation portion disposed between the igniter and the piston portion and configured to store a secondary ejection energy, the energy accumulation portion configured to directly receive the primary ejection energy from the igniter and then release the stored secondary ejection energy based on the received primary ejection energy, the secondary ejection energy not being a combustion based energy and configured to push the piston portion such that the substance is ejected from the encapsulating portion toward the target region.

2. The injector according to claim 1, wherein the application of the secondary ejection energy is configured to be caused by breakage of a part of the energy accumulation portion by the discharged combustion product.

3. The injector according to claim 1, wherein an ejection pressure of the substance intended for injection, which is defined as a pressure of the substance intended for injection ejected from the injector, is configured to be raised to a first peak pressure by application of the primary ejection energy by the igniter after the energy application is started, and then lowered to a pressure lower than the first peak pressure, and raised again to a second peak pressure by application of the secondary ejection energy.

4. The injector according to claim 1, wherein the energy accumulation portion includes:
  a filling space filled with a compressed gas that is compressed to a predetermined pressure; and
  a plate member configured to prevent contact between the compressed gas in the filling space and the piston portion prior to receiving the primary ejection energy and to be broken by the discharged combustion product, and
  as the discharged combustion product breaks the plate member, the compressed gas filled in the filling space is configured to be discharged to an outside of the filling space and come into contact with the piston portion, such that application of the secondary ejection energy is performed.

5. The injector according to claim 1, wherein the energy accumulation portion includes:
  a filling space filled with a compressed gas that is compressed to a predetermined pressure; and
  a regulation member configured to regulate advancement of the piston portion to the substance intended for injection,
  before application of the primary ejection energy by the igniter, the compressed gas in the filling space is configured to come into contact with the piston portion, and advancement of the piston portion is configured to be regulated by the regulation member, and
  after the primary ejection energy is applied by the igniter, the regulation member is configured to be broken, such that application of the secondary ejection energy is performed via the compressed gas.

6. The injector according to claim 1, wherein the energy accumulation portion includes:
  a predetermined space in which an end of the piston portion is exposed;
  a filling container filled with a compressed gas compressed to a predetermined pressure in an inside thereof in a state in which an opening thereof is sealed by a sealing member; and
  a penetrating member disposed to face the sealing member and configured to enable both the inside and an outside of the filling container to communicate with each other by penetration through the sealing member,
  before application of the primary ejection energy by the igniter, the compressed gas is stored in the filling container, and
  when the combustion product is discharged, the igniter is configured to apply the primary ejection energy to the substance intended for injection via the piston portion and the inside and the outside of the filling container are configured to be made to communicate with each other via the penetrating member by pressing the penetrating member against the sealing member, and then application of the secondary ejection energy is configured to be performed via the compressed gas that is discharged from the filling container.

7. The injector according to claim 1, wherein the energy accumulation portion includes:
- an elastic member being in a compressed state and disposed in a state of being in contact with the piston portion; and
- a regulation member configured to regulate advancement of the piston portion to the substance intended for injection, before application of the primary ejection energy by the igniter, advancement of the piston portion is configured to be regulated by the regulation member, and after the primary ejection energy is applied by the igniter, the regulation member is configured to be broken, such that application of the secondary ejection energy is performed by an elongated action of the elastic member.

8. The injector according to claim 1, wherein the secondary ejection energy is based on elastic force or non-combustion compressed gas.

9. The injector according to claim 1, wherein the energy accumulation portion comprises a gas chamber containing a compressed gas and a first plate member physically separating the gas chamber from the igniter, wherein the first plate member is configured to be broken upon receiving the discharged combustion product, and wherein the energy accumulation portion is configured to release the compressed gas as the secondary ejection energy so as to push the piston portion.

10. The injector according to claim 9, wherein the energy accumulation portion further comprises a second plate member sealing the gas chamber together with the first plate member and physically separating the gas chamber from the piston portion, wherein the second plate member is configured to be broken upon receiving the discharged combustion product, and wherein the energy accumulation portion is configured to release the compressed gas as the secondary ejection energy so as to push the piston portion.

* * * * *